(12) United States Patent
Pau et al.

(10) Patent No.: US 7,833,788 B2
(45) Date of Patent: Nov. 16, 2010

(54) PRODUCTION OF VACCINES

(75) Inventors: Maria Grazia Pau, Leiden (NL); Alphonsus G. C. M. UytdeHaag, Vleuten (NL)

(73) Assignee: Crucell Holland B.V., Leiden (NL)

( * ) Notice: Subject to any disclaimer, the term of this patent is extended or adjusted under 35 U.S.C. 154(b) by 0 days.

(21) Appl. No.: 12/454,095

(22) Filed: May 12, 2009

(65) Prior Publication Data
US 2009/0239287 A1  Sep. 24, 2009

Related U.S. Application Data

(62) Division of application No. 11/450,038, filed on Jun. 8, 2006, now Pat. No. 7,550,284, which is a division of application No. 09/449,854, filed on Nov. 26, 1999, now Pat. No. 7,192,759.

(51) Int. Cl.
C12N 5/071 (2010.01)
C12N 5/073 (2010.01)
C12N 5/10 (2006.01)
C12N 7/01 (2006.01)

(52) U.S. Cl. .............. 435/366; 435/235.1; 435/325
(58) Field of Classification Search .............. None
See application file for complete search history.

(56) References Cited

U.S. PATENT DOCUMENTS

| | | | |
|---|---|---|---|
| 4,703,008 A | 10/1987 | Lin |
| 4,835,260 A | 5/1989 | Shoemaker |
| 5,047,335 A | 9/1991 | Paulson et al. |
| 5,192,539 A | 3/1993 | Van Der Marel et al. |
| 5,441,868 A | 8/1995 | Lin |
| 5,457,089 A | 10/1995 | Fibi et al. |
| 5,494,790 A | 2/1996 | Sasaki et al. |
| 5,518,913 A | 5/1996 | Massie et al. |
| 5,631,158 A | 5/1997 | Dorai et al. |
| 5,714,587 A | 2/1998 | Laine |
| 5,767,078 A | 6/1998 | Johnson et al. |
| 5,773,569 A | 6/1998 | Wrighton et al. |
| 5,789,247 A | 8/1998 | Ballay et al. |
| 5,830,851 A | 11/1998 | Wrighton et al. |
| 5,835,382 A | 11/1998 | Wilson et al. |
| 5,856,292 A | 1/1999 | Thomas et al. |
| 5,856,298 A | 1/1999 | Strickland |
| 5,994,128 A | 11/1999 | Fallaux et al. |
| 6,033,908 A | 3/2000 | Bout et al. |
| 6,395,519 B1 | 5/2002 | Fallaux et al. |
| 6,413,746 B1 | 7/2002 | Field |
| 6,475,753 B1 | 11/2002 | Ruben et al. |
| 6,492,169 B1 | 12/2002 | Vogels et al. |
| 6,506,598 B1 | 1/2003 | Andersen et al. |
| 6,558,948 B1 | 5/2003 | Kochanek et al. |
| 6,653,101 B1 | 11/2003 | Cockett et al. |
| 6,855,544 B1 | 2/2005 | Hateboer et al. |
| 6,878,549 B1 | 4/2005 | Vogels et al. |
| 7,125,706 B2 | 10/2006 | Zhang et al. |
| 7,297,680 B2 | 11/2007 | Opstelten et al. |
| 7,470,523 B2 | 12/2008 | Bout et al. |
| 7,491,532 B2 | 2/2009 | Bout et al. |
| 7,504,248 B2 | 3/2009 | Marzio et al. |
| 7,550,284 B2 | 6/2009 | Pau et al. |
| 2002/0116723 A1 | 8/2002 | Grigliatti et al. |
| 2003/0087437 A1 | 5/2003 | Asada et al. |
| 2003/0092160 A1 | 5/2003 | Bout et al. |
| 2005/0164386 A1 | 7/2005 | Uytdehaag et al. |
| 2005/0170398 A1 | 8/2005 | Van Berkel et al. |
| 2007/0231860 A1 | 10/2007 | UytdeHaag et al. |
| 2007/0298464 A1 | 12/2007 | Opstelten et al. |

(Continued)

FOREIGN PATENT DOCUMENTS

| | | |
|---|---|---|
| EP | 0 411 678 | 2/1991 |
| EP | 0 185 573 | 6/1995 |
| EP | 0 833 934 B1 | 4/1998 |
| EP | 1 108 787 B1 | 6/2001 |
| WO | WO 93/03163 | 2/1993 |
| WO | WO 95/05465 | 2/1995 |

(Continued)

OTHER PUBLICATIONS

Alkhatib et al., "Expression of Bicistronic Measles Virus P/C mRNA by Using Hybrid Adenovirus: Levels of C Protein Synthesized In Vivo Are Unaffected by the Presence or Absence of the Upstream P Initiator Codon," Journal of Virology, Nov. 1988, pp. 4059-4068, vol. 62, No. 11.

(Continued)

*Primary Examiner*—Mary E Mosher
*Assistant Examiner*—Myron G Hill
(74) *Attorney, Agent, or Firm*—TraskBritt

(57) ABSTRACT

Means and methods are provided for the production of mammalian viruses comprising: infecting a culture of immortalized human cells with the virus, incubating the culture infected with virus to propagate the virus under conditions that permit growth of the virus, and to form a virus-containing medium, and removing the virus-containing medium. The viruses can be harvested and be used for the production of vaccines. Advantages are that human cells of the present invention can be cultured under defined serum free conditions, and the cells show improved capability for propagating virus. In particular, methods are provided for producing, in cultured human cells, influenza virus and vaccines derived thereof. This method eliminates the necessity to use whole chicken embryos for the production of influenza vaccines. The method provides also for the continuous or batchwise removal of culture media. As such, the invention allows the large-scale, continuous production of viruses to a high titer.

5 Claims, 7 Drawing Sheets

U.S. PATENT DOCUMENTS

| | | | |
|---|---|---|---|
| 2008/0050403 | A1 | 2/2008 | Marzio et al. |
| 2008/0131461 | A1 | 6/2008 | Pau et al. |
| 2009/0170164 | A1 | 7/2009 | Bout et al. |
| 2009/0285879 | A1 | 11/2009 | Pau et al. |
| 2009/0324645 | A1 | 12/2009 | Pau et al. |
| 2010/0015176 | A1 | 1/2010 | Havenga et al. |

FOREIGN PATENT DOCUMENTS

| | | |
|---|---|---|
| WO | WO 95/29994 | 11/1995 |
| WO | WO 97/00326 | 1/1997 |
| WO | WO 97/18318 | 5/1997 |
| WO | WO 98/18926 | 5/1998 |
| WO | WO 98/39411 | 9/1998 |
| WO | WO 98/44141 | 10/1998 |
| WO | WO 99/05268 | 2/1999 |
| WO | WO 99/24068 | 5/1999 |
| WO | WO 00/61164 | 10/2000 |
| WO | WO 00/63403 | 10/2000 |
| WO | WO 01/05945 A2 | 1/2001 |
| WO | WO 01/38362 A2 | 5/2001 |
| WO | WO0188117 A2 | 11/2001 |
| WO | WO 02/18948 | 3/2002 |
| WO | WO 02/053580 | 7/2002 |
| WO | WO 03/038100 A1 | 5/2003 |
| WO | WO 03/048197 A1 | 6/2003 |
| WO | WO 03/048348 A2 | 6/2003 |
| WO | WO 03/051927 | 6/2003 |
| WO | WO 2004/003176 | 1/2004 |
| WO | WO 2004/099396 | 11/2004 |

OTHER PUBLICATIONS

Alkhatib et al., "High-Level Eurcaryotic In Vivo Expression of Biologically Active Measles Virus Hemagglutinin by Using an Adenovirus Type 5 Helper-Free Vector System," Journal of Virology, Aug. 1988, pp. 2718-2727, vol. 62, No. 8.
Berg et al., High-Level Expression of Secreted Proteins from Cells Adapted to Serum-Free Suspension Culture, Research Report, 1993, pp. 972-978, vol. 14, No. 6.
Bout et al., "Improved helper cells for RCA-free production of E1-deleted recombinant adenovirus vectors," Cancer Gene Therapy, 1996, pp. S24, vol. 3, No. 6.
Bout et al., "Production of RCA-free batches of E1-deleted recombinant adenoviral vectors on PER.C6," Nucleic Acids Symp. Ser. 1998, XP-002115716, pp. 35-36.
Boutl et al., A novel packaging cell line (PER.C6) for efficient production of RCA-free batches of E1-deleted recombinant adenoviral vectors, Cancer Gene Therapy, 1997, pp. S32-S33, vol. 4, No. 6.
Brown et al., "Evaluation of Cell Line 293 for Virus isolation in Routine Viral Diagnosis," Journal of Clinical Microbiology, Apr. 1986, pp. 704-708, vol. 23, No. 4.
Bukreyev et al., "Recombinant Respiratory Syncytial Virus from Which the Entire SH Gene Has Been Deleted Grows Efficiently in Cell Culture and Exhibits Site-Specific Attenuation in the Respiratory Tract of the Mouse," Journal of Virology, Dec. 1997, pp. 8973-8982, vol. 71, No. 12.
Caravokyri et al., "Constitutive Episomal Expression of Polypeptide IX (pIX) in a 293-Based Cell Line Complements that Deficiency of pIX Mutant Adenovirus Type 5," Journal of Virology, Nov. 1995, pp. 6627-6633, vol. 69, No. 11.
Carroll et al., Abstract, Differential Infection of Receptor-modified Host Cells by Receptor-Specific Influenza Viruses, Virus Research, Sep. 1985, pp. 165-179, vol. 3, No. 2.
Certificate of deposit of the PER.C6 cell line (ECACC deposit under No. 96022940), 2001.
Ciccarone et al., "Lipofectamine 2000 Reagent for Transfection of Eukaryotic Cells," Focus, 1999, pp. 54-55, vol. 21, No. 2.
Cote et al., Serum-Free Production of Recombinant Proteins and Adenoviral Vectors by 293SF-3F6 Cells, Biotechnology and Bioengineering, Sep. 5, 1998, pp. 567-575, vol. 59, No. 5.
Cronan, Abstract, Biotination of Proteins in-vivo a post-translational modification to label purify and study proteins, Journal of Biological Chemistry, Jun. 25, 1990, pp. 10327-10333, vol. 265, No. 18.
DuBridge et al., "Analysis of Mutation in Human Cells by Using an Epstein-Barr Virus Shuttle System," Molecular and Cellular Biology, Jan. 1987, pp. 397-387, vol. 7, No. 1.
Endo et al.. Growth of Influenza A Virus in Primary, Differentiated Epithelial Cells Derived from Adenoids, Journal of Virology, Mar. 1996, pp. 2055-2058, vol. 70, No. 3.
Fallaux et al, "New helper cells and matched early region 1-deleted adenovirus vectors prevent generation of replication-competent adenoviruses," Human Gene Therapy, Sep. 1, 1998, vol. 9, No. 1, pp. 1909-1917.
Fallaux et al., Characterization of 911: A New Helper Cell Line for the Titration and Propagation of Early Region 1-Deleted Adenoviral Vectors, Human Gene Therapy, Jan. 20, 1996, pp. 215-222, vol. 7.
Figure 1 submitted by Opponent I.
Gallimore et al., Transformation of Human Embryo Retinoblasts with Simian Virus 40, Adenovirus and ras Oncogenes, Anticancer Research, 1986, pp. 499-508, vol. 6.
Garnier et al., Scale-up of the adenovirus expression system for the production of recombinant protein in human 293S cells, Cytotechnology, 1994, pp. 145-155, vol. 15.
GenBank Accession No. X02996.1, 1993, "Adenovirus type 5 left 32% of the genome."
Ghosh-Choudhury et al., Protein IX, a minor component of the human adenovirus capsid, is essential for the packaging of the full length genomes, The EMBO Journal, 1987, pp. 1733-39, vol. 6, No. 6.
GIBCO cell culture, A Guide to Serum-Free Cell Culture, www.invitrogen.com.
Grabenhorst et al., Construction of stable BHK-21 cells coexpressing human secretory glycoproteins and human Gal(beta-1-4)GlcNAc-R alpha-2,6-sialyltransferase alpha-2,6-Linked NeuAc is preferentially attached to the Gal(beta-1-4)GlcNAc(beta-1-2)Man(alpha-1-3)-branch of diantennary oligosaccharides from secreted recombinant beta-trace protein, Eur. J. Biochem, 1995, pp. 718-725, vol. 232, No. 3, Berlin, Germany.
Graham et al., "Characteristics of a Human Cell Line Transformed by DNA from Human Adenovirus Type 5," J. Gen. Virol., 1977, pp. 59-72, vol. 36.
Graham et al., "Growth of 293 cells in suspension culture," J Gen Virol, Mar. 1987, pp. 937-940, vol. 68.
Graham, Cell Lines, Promochem (visited Apr. 10, 2005) <http://www.lgcpromochem-atcc.com/SearchCatalogs/longview.cfm?view=ce,1146678...>.
Grand et al., "Modulation of the level of expression of cellular genes in adenovirus 12-infected and transformed human cells," Eur Mol Biol Organ J. 1986, 5 (6) 1253-1260, Abstract.
Grand et al., "The high levels of p53 present in adenovirus early region 1-transformed human cells do not cause up-regulation of MDM2 expression," Virology, 1995, vol. 210, No. 2, pp. 323-334, Abstract.
Hollister et al., Stable expression of mammalian beta1,4-galactosyltransferase extends the N-glycosylation pathway in insect cells, Glycobiology, 1998, pp. 473-480, vol. 8, No. 5, IRL Press, United Kingdom.
Holzer et al.. "Construction of a Vaccinia Virus Deficient in the Essential DNA Repair Enzyme Uracil DNA Glycosylase by a Complementing Cell Line," Journal of Virology, Jul. 1997, pp. 4997-5002, vol. 71, No. 7.
Inoue et al., Production of Recombinant Human Monoclonal Antibody Using ras-Amplified BHK-21 Cells in a Protein-free Medium, Biosci. Biotech. Biochem., 1996, pp. 811-817, vol. 60, No. 5.
Interlocutory Decision of the Opposition Division of Jul. 21, 2003 in the case EP 0 695 351(European application 94 913 174.2).
Jenkins et al., Getting the glycosylation right: Implications for the biotechnology industry, Nature Biotechnology, Aug. 1996, pp. 975-981, vol. 14, No. 8, Nature Publishing, US.
Lopez et al., Efficient production of biologically active human recombinant proteins in human lymphoblastoid cells form integrative and episomal expression vectors, Gene, 1994, pp. 285-291, vol. 148.

Louis et al., Cloning and Sequencing of the Cellular—Viral Junctions from the Human Adenovirus Type 5 Transformed 293 Cell Line, Virology, 1997, pp. 423-429, vol. 233.

Lutz et al., "The Product of the Adenovirus Intermediate Gene IX Is a Transcriptional Activator," Journal of Virology, Jul. 1997, pp. 5102-5109, vol. 71, No. 7.

Manservigi et al., "Protection from Herpes Simplex Virus Type 1 Lethal and Latent Infections by Secreted Recombinant Glycoprotein B Constitutively Expressed in Human Cells with a BK Virus Episomal Vector," Journal of Virology, Jan. 1990, pp. 431-436, vol. 64, No. 1.

Marketing Authorization and Scientific Discussion for Xigris.

Massie et al., Improved Adenovirus Vector Provides Herpes Simplex Virus Ribonucleotide Reductase R1 and R2 Subunits Very Efficiently, Biotechnology, Jun. 1995, pp. 602-608, vol. 13.

Merten et al., Production of Influenza Virus in Cell Cultures for Vaccine Preparation, Exp Med Biol., 1996, pp. 141-151, vol. 397.

Minch et al., Tissue Plasminogen Activator Coexpressed in Chinese Hamster Ovary Cells with alpha(2,6)-Sialyltransferase Contains NeuAc-alpha(2,6)Gal-beta(1,4)Glc-N-AcR Linkages, Biotechnol. Prog., 1995, pp. 348-351, vol. 11, No. 3.

NCBI Entrez Nucleotide accession No. NC_002018.

NCBI Entrez Nucleotide accession No. U38242.

NCBI Entrez Nucleotide accession No. X02996 J01967 J01968 J01970 J01971 J01972 J01974 J01976 J01977 J01978 J01979 K00515 V00025 V00026 V00027 V00029.

Neumann et al., "Generation of influenza A viruses entirely from cloned cDNAs," Proc. Natl. Acad. Sci., Aug. 1999, pp. 9345-9350, vol. 96.

Notice of Opposition to a European Patent for 1 161 548.

Opposition against European patent 1 108 878 B1 filed Oct. 5, 2005 in the name and on behalf of CEVEC Pharmaceuticals GmbH.

Opposition against European patent 1 161 548 B1 filed Nov. 16, 2005, in the name and on behalf of CEVEC Pharmaceutical GmbH.

Opposition against European patent 1108787 filed Oct. 5, 2005 in the name and on behalf of Probiogen AG.

Ory et al., "A stable human-derived packaging cell line for production of high titer retrovirus/vesicular stomatitis virus G pseudotypes," Proc. Natl. Acad. Sci., Oct. 1996, pp. 11400-11406, vol. 93.

Pacitti et al., Inhibition of Reovirus Type 3 Binding to Host Cells by Sialylated Glycoproteins Is Mediated through the Viral Attachment Protein, Journal of Virology, May 1987, pp. 1407-1415, vol. 61, No. 5, American Society for Microbiology.

Parkinson et al., "Stable Expression of a Secretable Deletion Mutant of Recombinant Human Thrombomodulin in Mammalian Cells," The Journal of Biological Chemistry, Jul. 25, 1990, pp. 12602-12610, vol. 265, No. 21.

Pau et al., Abstract, The human cell line Per.C6 provides a new manufacturing system for the production of influenza vaccines, Vaccine, Mar. 21, 2001, pp. 2716-2721, vol. 19, No. 17-19.

Paul et al., Increased Viral Titer Through Concentration of Viral Harvests from Retroviral Packaging Lines, Human Gene Therapy, 1993, pp. 609-615, vol. 4.

Pazur et al., Abstract, Oligosaccharides as immunodeterminants of erythropoietin for two sets of anti-carbohydrate antibodies, Journal of Protein Chemistry, Nov. 2000, pp. 631-635, vol. 19, No. 8.

PCT International Preliminary Examination Report and Written Opinion, PCT/NL00/00862, dated Apr. 8, 2002.

PCT International Search Report, PCT/NL00/00862, dated Jul. 4, 2001.

Pleschka et al., "A Plasmid-Based Reverse Genetics System for Influenza A Virus," Journal of Virology, Jun. 1996, pp. 4188-4192, vol. 70, No. 6.

PubMed listing of abstracts (visited Apr. 10, 2005) <http://www.ncbi.nlm.nih.gov/entrez/query.fcgi?CMD=search&DB=pubmed.

Reina et al., Comparison of Madin-Darby Canine Kidney cells (MDCK) with a Green Monkey Continuous Cell Line (Vero) and Human Lung Embryonated Cells (MRC-5) in the Isolation of Influenza A Virus from Nasopharyngeal Aspirates by Shell Vial Culture, Journal of Clinical Microbiology, Jul. 1997, pp. 1900-1901, vol. 35, No. 7.

Rhim et al., "Development of Human Cell Lines from Multiple Organs," Annals of the New York Academy of Sciences, 2000, pp. 16-25, vol. 919.

Schiedner et al., Abstract, Efficient transformation of primary human amniocytes by E1 functions of Ad5: generation of new cell lines for adenoviral vector production, 2000, Hum. Gene Ther. 11, 2105-2116.

Setoguchi et al., "Stimulation of Erythropoiesis by in vivo gene therapy: Physiologic consequences of transfer of the humanerythropoietin gene to experimental animals using an adenovirus vector," Blood, Nov. 1, 1994, pp. 2946-2953, vol. 84, No. 9.

Shultz-Cherry et al., "Mink Lung Epithelial Cells: Unique Cell Line That Supports Influenza A and B Virus Replication," Journal of Clinical Microbiology, Dec. 1998, pp. 3718-3720, vol. 36.

Spector et al., "Regulation of Integrated Adenovirus Sequences During Adenovirus Infection of Transformed Cells," Journal of Virology, Dec. 1980, pp. 860-871, vol. 36, No. 3.

Stevens et al., "The N-Terminal Extension of the Influenza B Virus Nucleoprotein Is Not Required for Nuclear Accumulation or the Expression and Replication of a Model RNA," Journal of Virology, Jun. 1998, pp. 5307-5312, vol. 72, No. 6.

Stockwell et al., High-throughput screening of small molecules in Miniaturized Mammalian Cell-based Assays involving Post-translational Modifications, Chemistry and Biology, Feb. 1999, pp. 71-83, vol. 6, No. 2.

U.S. Department of Health and Human Services, Public Health Service, Food and drug Administration, Center for Biologics Evaluation and Research, International Association for Biologicals, National Institute of Allergy and Infectious Diseases, National Vaccine Program Office, World Health Organization, Evolving Scientific and Regulatory Perspectives on Cell Substrates for Vaccine Development, Workshop, Friday, Sep. 10, 1999 (visited Sep. 30, 2005) <http://www.fda.gov.cber.minutes/0910evolv.txt>.

Weikert et al., Engineering Chinese hamster ovary cells to maximize sialic acid content of recombinant glycoproteins, Nature Biotechnology, Nov. 1999, pp. 1116-1121, vol. 17, No. 11, Nature Pub. Co., New York, NY, US.

Yan et al., Novel Asn-linked oligosaccharides terminating in GalNAcbeta(1-4)[Fucalpha(1-3)]GlcNAcbeta(1-.) are present in recombinant human Protein C expressed in human kidney 293 cells, Glycobiology, 1993, pp. 597-608, vol. 3. No. 6.

Yeager et al., Constructing immortalized human cell lines, Current Opinion Biotechnology, 1999, pp. 465-469, vol. 10.

Yeh et al., Adenoviral Vectors, pp. 25-42 of "Concepts in Gene Therapy," Publisher Walter de Gruyter, New York.

Yu et al., "Enhanced c-erbB-2/neu expression in human ovarian cancer cells correlates with more severe malignancy that can be suppressed by E1A," Cancer Res., 1993, 53 (4) 891-8. Abstract.

Zhang et al., Stable expression of human alpha-2,6-sialyltransferase in Chinese hamster ovary cells: functional consequences for human erythropoietin expression and bioactivity, BBA—General Subjects, 1998, pp. 441-452, vol. 1425, No. 3, Elsevier Science Publishers, NL.

Yallop et al., "PER.C6® Cells for the Manufacture of Biopharmaceutical Proteins," Modern Biopharmaceuticals, Ed. J. Knablein, 2005, Wiley-VCH Verlag GmbH & Co. KGaA, Weinheim, Germany.

Summons to attend Oral Proceedings by the EPO for Patent No. 1108787, dated Mar. 7, 2007.

Letter from von Kreisler Selling Werner dated Dec. 21, 2007 in opposition against EP 1108787/00204190.3-2405.

Letter from Dehmel & Bettenhausen (on behalf of Cevec Pharmaceuticals GmbH) dated Dec. 21, 2007 in opposition against EP 1108787 B1 (00 204 190.3) with enclosure.

Patience et al., Infection of human cells by an endogenous retrovirus of pigs, Nature Medicine, vol. 3, 1997, pp. 282-286.

Davis et al., Microbiology, Lippincott Company, Fourth Edition, 1990, p. 770.

Letter from Vossius & Partner dated Dec. 21, 2007 in opposition against EP 00204190.3/1108787 with enclosures.

Declaration of Dr. Uytdehaag signed Dec. 20, 2007 with attachments.

Hoffmann et al., A DNA transfection system for generation of influenza A virus from eight plasmids, PNAS, May 23, 2000, vol. 97, No. 11, pp. 6108-6113.

U.S. Appl. No. 11/026,518, filed Dec. 30, 2004, Uytdehaag et al., Overexpression of Enzymes Involved in Post-Translational Protein Modifications in Human Cells.

U.S. Appl. No. 11/105,725, filed Apr. 14, 2005, Havenga et al., New Settings for Recombinant Adenoviral-Based Vaccines.

U.S. Appl. No. 11/450,038, filed Jun. 8, 2006, Pau et al., Production of Vaccines.

U.S. Appl. No. 11/665,393, filed Apr. 13, 2007, Pau et al., Malaria Prime/Boost Vaccines.

U.S. Appl. No. 11/731,246, filed Mar. 30, 2007, UytdeHaag et al., Overexpression of Enzymes Involved in Post-Translational Protein Modifications in Human Cells.

U.S. Appl. No. 11/821,107, Jun. 20, 2007, Opstelten et al., Compositions of Erythropoietin Isoforms Comprising Lewis-X Structures and High Sialic Acid Content.

U.S. Appl. No. 11/879,422, filed Jul. 16, 2007, Marzio et al., Production of Viruses, Viral Isolates and Vaccines.

U.S. Appl. No. 11/975,396, filed Oct. 18, 2007, Pau et al., Recombinant Viral-Based Malaria Vaccines.

U.S. Appl. No. 12/220,971, filed Jul. 29, 2008, UytdeHaag et al., Vaccines Against West Nile Virus.

U.S. Appl. No. 12/291,881, filed Nov. 14, 2008, Hateboer et al., Recombinant Protein Production in a Human Cell.

U.S. Appl. No. 12/317,508, filed Dec. 23, 2008, Pau et al., Malaria Prime/Boost Vaccines.

U.S. Appl. No. 12/380,095, filed Feb. 24, 2009, Pau et al., Production of Vaccines.

Berg et al.. E1a-responsive mammalian host-vector system for the stable high-level expression of secreted proteins, Nucleic Acids Research, 1992, pp. 5485-5486, vol. 20, No. 20.

Bout et al., "PER.C6 as production platform for human monoclonal antibodies," Human Antibodies, Oct. 8, 2003, pp. 30, vol. 12, No. 1-2.

Chitlaru et al., Biochem., J., 1998, pp. 647-658, vol. 336.

Jones et al., "High-Level Expression of Recombinant IgG in the Human Cell Line PER.C6," Biotechnology Progress, Jan. 14, 2003, pp. 163-168, vol. 19.

Jones et al., "PER.C6 Cell Line for Human Antibody Production: Crucell's Technology Maintains 'Human' Glycoylation Patterns," Genetic Engineering News, May 15, 2002, pp. 50, 54, vol. 80, No. 5.

Kurokawa et al., Biotech. Bioeng. 1994, vol. 44, pp. 95-103.

Matsumoto et al., Characterization of a Human Glycoprotein (Erythropoietin) Produced in Cultured Tobacco Cells, Plant Mol. Biol., 1995, vol. 27, pp. 1163-1172.

PCT International Preliminary Report, PCT/EP2004/050724, dated Jan. 27, 2005.

PCT International Search Report, PCT/EP2004/050724, dated Oct. 1, 2004.

PCT International Search Report, PCT/NL02/00804, dated Sep. 26, 2003.

Pham et al., Abstract, "Large-Scale Transient Transfection of Serum-Free Suspension-Growing HEK293 EBNA1 Cells: Peptone Additives Improve Cell Growth and Transfection Efficiency," Biotechnology and Bioengineering, Nov. 5, 2003, pp. 332-342, vol. 84, No. 3.

Trudel et al., Process Biochemistry Jan./Feb. 1983, pp. 2-4 and 9.

Varki et al., Essentials of glycobiology, 1999, Cold Spring harbor Laboratory Press, Cold Spring Harbor, New York.

Walls et al., Amplification of multicistronic plasmids in the human 293 cell line and secretion of correctly processed recombinant human protein C, Gene, 1989, pp. 139-149, vol. 81.

Xie et al., "Large-Scale Propagation of a Replication-Defective Adenovirus Vector in Stirred-Tank Bioreactor PER.C6 Cell Culture Under Sparging Conditions," Jul. 5, 2003, Biotechnology and Bioengineering, pp. 45-52, vol. 83, No. 1.

Xie et al., "Serum-Free Suspension Cultivation of PER.C6 Cells and Recombinant Adenovirus Production Under Different pH Conditions," Biotechnology and Bioengineering, Dec. 5, 2002, pp. 569-579, vol. 80, No. 5.

Yatsiv et al., Erythropoietin is Neuroprotective, Improves Functional Recovery, and Reduces Neuronal Apoptosis and Inflammation in a Rodent Model of Experimental Closed Head Injury, Faseb J., 2005, vol. 19, pp. 1701-1703.

Office Action for U.S. Appl. No. 11/731,246, dated Oct. 2, 2009.

Office Action for U.S. Appl. No. 11/879,422, dated Oct. 2, 2009.

Office Action for U.S. Appl. No. 11/026,518, dated Jun. 15, 2007.

Office Action for U.S. Appl. No. 11/026,518, dated Jan. 12, 2009.

Office Action for U.S. Appl. No. 11/026,518, dated Jul. 21, 2009.

PRODUCTION OF VACCINES

CROSS-REFERENCE TO RELATED APPLICATIONS

This application is a divisional of U.S. patent application Ser. No. 11/450,038, filed Jun. 8, 2006, now U.S. Pat. No. 7,550,284, which is a divisional of U.S. patent application Ser. No. 09/449,854, filed Nov. 26, 1999, now U.S. Pat. No. 7,192,759, issued Mar. 20, 2007, the contents of each of which are incorporated herein by this reference.

TECHNICAL FIELD

The invention relates to biotechnology and the development and manufacture of vaccines. In particular, the invention relates to the field of production of viral proteins and/or viruses, more in particular to the use of a mammalian cell, preferably a human cell for the production of viruses growing in eukaryotic, preferably mammalian and, in particular, human cells. The invention is particularly useful for the production of vaccines to aid in protection against viral pathogens for vertebrates, in particular mammalians and especially humans.

BACKGROUND

Means and methods are disclosed herein for producing a virus and/or viral protein in a (human) cell, preferably using a defined synthetic medium, and for purifying the virus and/or components thereof from the cell and/or culture medium. Pharmaceutical compositions containing virus or its components and methods for manufacturing and recovering and/or purifying them are provided.

Vaccination is the most important route of dealing with viral infections. Although a number of antiviral agents are available, typically these agents have limited efficacy. Administering antibodies against a virus may be a good way of dealing with viral infections once an individual is infected (passive immunization) and typically human or humanized antibodies do seem promising for dealing with a number of viral infections. But the most efficacious and safe way of dealing with virus infection is, and probably will be, prophylaxis through active immunizations. Active immunization is generally referred to as vaccination and vaccines comprising at least one antigenic determinant of a virus, preferably a number of different antigenic determinants of at least one virus, e.g., by incorporating in the vaccine at least one viral polypeptide or protein derived from a virus (subunit vaccines). Typically, the formats mentioned so far include adjuvants in order to enhance an immune response. This also is possible for vaccines based on whole virus, e.g., in an inactivated format. A further possibility is the use of live, but attenuated forms of the pathogenic virus. A further possibility is the use of wild-type virus, e.g., in cases where adult individuals are not in danger from infection, but infants are and may be protected through maternal antibodies and the like. Production of vaccines is not always an easy procedure. In some cases the production of viral material is on eggs, which leads to difficulty in purifying material and extensive safety measures against contamination, etc. Also production on bacteria and or yeasts, which sometimes, but not always, is an alternative for eggs, requires many purification and safety steps. Production on mammalian cells would be an alternative, but mammalian cells used so far all require, for instance, the presence of serum and/or adherence to a solid support for growth. In the first case, again, purification and safety and e.g., the requirement of protease to support the replication of some viruses become an issue. In the second case, high yields and ease of production become a further issue. The present invention overcomes at least a number of the problems encountered with the production systems for production of viruses and/or viral proteins for vaccine purposes of the systems of the prior art.

BRIEF SUMMARY OF THE INVENTION

Thus, in certain aspects, the invention provides a method for producing a virus and/or viral proteins, other than adenovirus or adenoviral proteins, for use as a vaccine comprising providing a cell with at least a sequence encoding at least one gene product of the E1 gene or a functional derivative thereof of an adenovirus, providing the cell with a nucleic acid encoding the virus or the viral proteins, culturing the cell in a suitable medium and allowing for propagation of the virus or expression of the viral proteins and harvesting the virus and/or viral proteins from the medium and/or the cell. Until the present invention, there were few, if any (human) cells that had been found suitable to produce viruses and/or viral proteins for use as vaccines in any reproducible and upscaleable manner and/or with sufficiently high yields and/or which were easily purifiable. We have now found that cells which comprise adenoviral E1 sequences, preferably in their genome, are capable of sustaining the propagation of viruses in significant amounts.

The preferred cell according to the invention is derived from a human primary cell, preferably a cell which is immortalized by a gene product of the E1 gene. In order to be able to grow a primary cell, of course, it needs to be immortalized. A good example of such a cell is one derived from a human embryonic retinoblast.

In cells according to the invention, it is important that the E1 gene sequences are not lost during the cell cycle. It is, therefore, preferred that the sequence encoding at least one gene product of the E1 gene is present in the genome of the (human) cell. For reasons of safety care, it is best taken to avoid unnecessary adenoviral sequences in the cells according to the invention. It is, thus, another embodiment of the invention to provide cells that do not produce adenoviral structural proteins. However, in order to achieve large-scale (continuous) virus production through cell culture, it is preferred to have cells capable of growing without needing anchorage. The cells of the present invention have that capability. To have a clean and safe production system from which it is easy to recover and, if desirable, to purify the virus, it is preferred to have a method according to the invention, whereby the human cell comprises no other adenoviral sequences. The most preferred cell for the methods and uses of the invention is PER.C6®, as deposited under the Budapest Treaty under ECACC No. 96022940, or a derivative thereof.

Thus, the invention provides a method of using a cell according to the invention, wherein the cell further comprises a sequence encoding E2A, or a functional derivative or analogue or fragment thereof, preferably, a cell wherein the sequence encoding E2A, or a functional derivative or analogue or fragment thereof is present in the genome of the human cell and, most preferably, a cell wherein the E2A encoding sequence encodes a temperature-sensitive mutant E2A.

Furthermore, as stated, the invention also provides a method according to the invention wherein the (human) cell is capable of growing in suspension.

The invention also provides a method wherein the human cell can be cultured in the absence of serum. The cells according to the invention, in particular PER.C6®, have the additional advantage that they can be cultured in the absence of serum or serum components. Thus, isolation is easy, safety is enhanced and reliability of the system is good (synthetic media are the best in reproducibility). The human cells of the invention and, in particular, those based on primary cells and particularly the ones based on HER cells, are capable of normal post- and peri-translational modifications and assembly. This means that they are very suitable for preparing viral proteins and viruses for use in vaccines.

Thus, the invention provides a method according to the invention, wherein the virus and/or the viral proteins comprise a protein that undergoes post-translational and/or peri-translational modification, especially wherein the modifications comprise glycosylation. A good example of a viral vaccine that has been cumbersome to produce in any reliable manner is influenza vaccine. The invention provides a method wherein the viral proteins comprise at least one of an Influenza virus neuramidase and/or a hemagglutinin. Other viral proteins (subunits) and viruses (wild-type to be inactivated) or attenuated viruses that can be produced in the methods according to the invention include enterovirus, such as rhinovirus, aphtovirus, or poliomyelitis virus, herpes virus, such as herpes symplex virus, pseudorabies virus or bovine herpes virus, orthomyxovirus, such as influenza virus, a paramyxovirus, such as Newcastle disease virus, respiratory syncitio virus, mumps virus or a measles virus, retrovirus, such as human immunedeficiency virus, or a parvovirus or a papovavirus, rotavirus or a coronavirus, such as transmissable gastroenteritis virus or a flavivirus, such as tick-borne encephalitis virus or yellow fever virus, a togavirus, such as rubella virus or eastern-, western-, or Venezuelean-equine encephalomyelitis virus, a hepatitis causing virus, such as hepatitis A or hepatitis B virus, a pestivirus, such as hog cholera virus, or a rhabdovirus, such as rabies virus.

The invention also provides the use of a human cell having a sequence encoding at least one E1 protein of an adenovirus or a functional derivative, homologue or fragment thereof, in its genome, which cell does not produce structural adenoviral proteins for the production of a virus, or at least one viral protein for use in a vaccine. Of course, for such a use the cells preferred in the methods according to the invention are also preferred. The invention also provides the products resulting from the methods and uses according to the invention, especially viral proteins and viruses obtainable according to those uses and/or methods, especially when brought in a pharmaceutical composition comprising suitable excipients and in some formats (inactivated viruses, subunits) adjuvants. Dosage and ways of administration can be sorted out through normal clinical testing in as far as they are not yet available through the already registered vaccines.

Thus, the invention also provides a virus or a viral protein for use in a vaccine obtainable by a method or by a use according to the invention, the virus or the viral protein being free of any non-human mammalian proteinaceous material, and a pharmaceutical formulation comprising such a virus and/or viral protein.

The invention further provides a human cell having a sequence encoding at least one E1 protein of an adenovirus or a functional derivative, homologue or fragment thereof, in its genome, which cell does not produce structural adenoviral proteins and having a nucleic acid encoding a virus or at least one non-adenoviral viral protein. This cell can be used in a method according to the invention.

In a preferred embodiment, the invention provides influenza virus obtainable by a method according to the invention or by a use according to the invention. In another embodiment the invention provides influenza vaccines obtainable by a method according to the invention or by a use according to the invention.

DETAILED DESCRIPTION OF THE INVENTION

Figure 1:
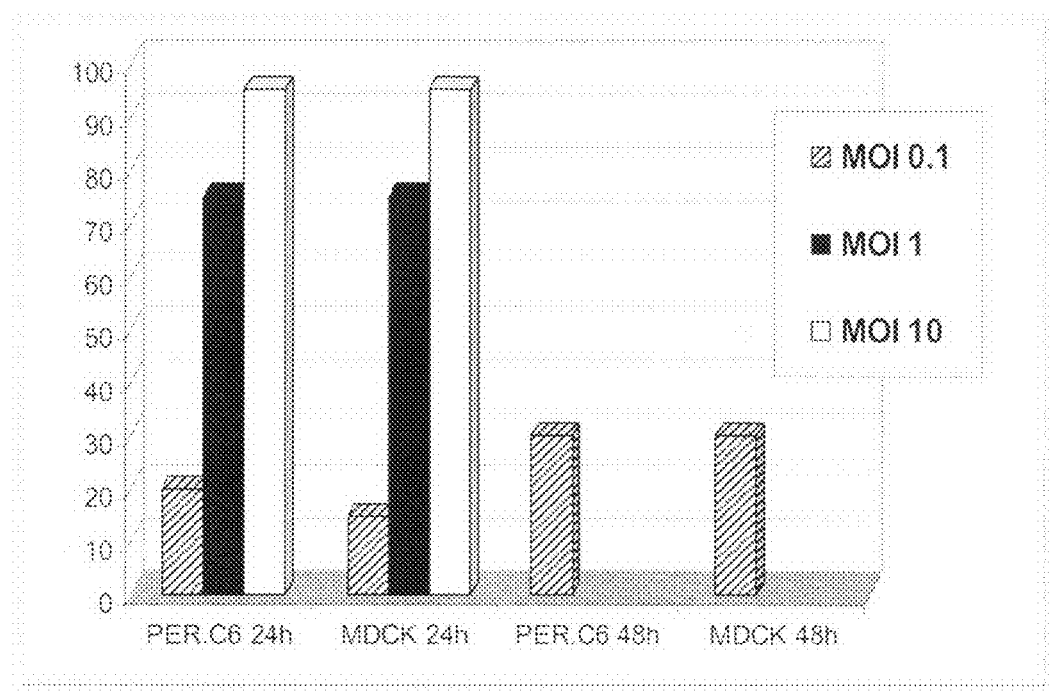
FIG. 1: Percentage of infected cells (positive cells) viewed microscopically after immunofluorescence assay versus percentage of dead cells measured via FACS after propidium iodide staining, at MOIs of 10-3 and 10-4. Poor viability of the cells from samples derived from infection at moi 10-3 didn't give rise to reliable data.

The present invention discloses a novel, human immortalized cell line for the purpose of propagating and harvesting virus, for production of the virus. PER.C6® cells (WO 97/00326) were generated by transfection of primary human embryonic retina cells, using a plasmid that contained the Ad serotype 5 (Ad5) E1A- and E1B-coding sequences (Ad5 nucleotides 459-3510 SEQ ID NO:1 of the incorporated herein SEQUENCE LISTING) under the control of the human phosphoglycerate kinase (PGK) promoter.

The following features make PER.C6®, or a derivative, particularly useful as a host for virus production: it is a fully characterized human cell line; it was developed in compliance with GLP; it can be grown as suspension cultures in defined serum-free medium, devoid of any human or animal serum proteins; and its growth is compatible with roller bottles, shaker flasks, spinner flasks and bioreactors, with doubling times of about 35 hours.

Influenza Epidemiology

Influenza viruses, members of the family of Orthomyxoviridae, are the causative agents of annual epidemics of acute respiratory disease. In the US alone, 50 million Americans get the flu each year. Estimated deaths worldwide (1972-1992) are 60,000 (CDC statistics). There have been three major cases of pandemic outbreaks of influenza, namely in 1918 (Spanish flu, estimated 40 million deaths), in 1957 (Asian flu, estimated one million deaths), and in 1968 (Hong-Kong flu, estimated 700,000 deaths). Infections with influenza viruses are associated with a broad spectrum of illnesses and complications that result in substantial worldwide morbidity and mortality, especially in older people and patients with chronic illness. Vaccination against influenza is most effective in preventing the often fatal complications associated with this infection (B. R. Murphy and R. G. Webster, 1996). The production of influenza virus on the diploid human cell line MRC-5 has been reported (L. Herrero-Euribe et al., 1983). However, the titers of influenza virus are prohibitively low.

Strains of Influenza Virus

Present day flu vaccines contain purified hemagglutinin and neuraminidase of influenza virus A and B. The three viruses that represent epidemiologically important strains are influenza A(H1N1), influenza A(H3N2) and influenza B. The division into A and B types is based on antigenic differences between their nucleoprotein (NP) and matrix (M) protein antigen. The influenza A virus is further subdivided into subtypes based on the antigenic composition (sequence) of hemagglutinin (H1-H15) and neuraminidase (N1-N9) molecules. Representatives of each of these subtypes have been isolated from aquatic birds, which probably are the primordial reservoir of all influenza viruses for avian and mammalian species. Transmission has been shown between pigs and humans and, recently, (H5N1) between birds and humans.

Influenza Vaccines

Three types of inactivated influenza vaccines are currently used in the world: whole virus, split product and surface antigen or subunit vaccines. These vaccines all contain the surface glycoproteins, hemagglutinin (HA) and neuraminidase (NA) of the influenza virus strains that are expected to circulate in the human population in the upcoming season.

These strains, which are incorporated in the vaccine, are grown in embryonated hens' eggs, and the viral particles are subsequently purified before further processing.

The need for the yearly adjustment of influenza vaccines is due to antigen variation caused by processes known as "antigenic drift" and "antigenic shift."

Antigenic drift occurs by the accumulation of a series of point mutations in either the H or N protein of a virus resulting in amino acid substitutions. These substitutions prevent the binding of neutralizing antibodies, induced by previous infection, and the new variant can infect the host.

Antigenic shift is the appearance of a new subtype by genetic reassortment between animal and human influenza A viruses. The pandemic strains of 1957 (H2N2) and 1968 (H3N2) are examples of reassorted viruses by which avian H and/or N genes were introduced in circulating human viruses, which subsequently could spread among the human population.

Based on the epidemiological surveys by over hundred National Influenza Centers worldwide, the World Health Organization (WHO) yearly recommends the composition of the influenza vaccine, usually in February for the Northern hemisphere, and in September for the Southern hemisphere. This practice limits the time window for production and standardization of the vaccine to a maximum of nine months.

In case of an urgent demand of many doses of vaccine, for example, when a novel subtype of influenza A virus arises by antigenic shift and antigenic drift, limited availability of eggs may hamper the rapid production of vaccine. Further disadvantages of this production system are the lack of flexibility, the risk of the presence of toxins and the risks of adventitious viruses, particularly retroviruses, and concerns about sterility. This presents a serious problem in today's practice of influenza vaccine production on embryonated hens' eggs.

Therefore, the use of a cell culture system for influenza vaccine production would be an attractive alternative. Influenza viruses can be grown on a number of primary cells, including monkey kidney, calf kidney, hamster kidney and chicken kidney. Yet, their use for vaccine production is not practical because of the need to re-establish cultures from these primary cells for each preparation of a vaccine. Therefore, the use of continuous cell lines for influenza vaccine production is an attractive alternative.

The use of culture systems was facilitated by the realization that the proteolytic cleavage of HA in its two subunits (HA1 and HA2), which is required for influenza virus infectivity, can be obtained by the addition of trypsin. Inclusion of trypsin permits replication and plaque formation in Madin-Darby canine kidney (MDCK) cells (K. Tobita et al., 1975).

The MDCK cell line was recently shown to support the growth of influenza virus for vaccine production (R. Brand et al., 1996, 1997; A. M. Palache et al., 1997). The use of trypsin requires growth of the MDCK cells in serum-free tissue culture medium (MDCK-SF1). However, MDCK cells are currently not approved as a substrate for production of influenza virus.

However, any non-human system for production of influenza vaccines has an inherent drawback known as "adaptation." Human influenza A and B virus both carry mutations in the HA, due to adaptation in embryonated hens' eggs. These mutations result in altered antigenicity (R. W. Newman et al., 1993; S. P. Williams and J. S. Robertson, 1993; J. S. Robertson et al., 1994; L. V. Gubareva et al., 1994; G. C. Schild et al., 1993; J. S. Robertson et al., 1987; S. Kodihalli et al., 1995). In humans, immunization with vaccines containing an HA bearing an egg-adaption mutation induces less neutralizing antibody to virus that contains a non-egg adapted HA (R. W. Newman et al., 1993).

Human influenza viruses propagated in canine cells such as MDCK cells also show adaptation, albeit to a lesser extent. Such viruses resemble the original human isolates more closely than egg-derived viruses (J. S. Robertson et al., 1990).

Furthermore, there is evidence that host-specific changes in NA and host-specific phosphorylation patterns of NP can affect the replication of influenza viruses (J. L. Schulman and P. Palese 1977; A. Sugiara and M. Ueda, 1980; 0. Kistner et al., 1976).

Therefore, it would clearly be advantageous to avoid adaptation or other host-induced changes of influenza virus. It may result in a more homogeneous population of viruses and render the ultimate vaccine more effective.

In certain embodiments, the invention provides human cells as a substrate for the production of high titers of influenza virus, suitable for the development of vaccines.

To illustrate the invention, the following illustrative examples are provided, not intended to limit the scope of the invention.

EXAMPLES

PER.C6®D Cell Banking

Cell line PER.C6® cell (deposited under No. 96022940 at the European Collection of Animal Cell Cultures at the Center for Applied Microbiology and Research), or derivatives thereof, were used (described in U.S. Pat. No. 5,994,128 to Fallaux et al., which is incorporated herein by this reference). Cell lines were banked by a two tier cell bank system. The selected cell line was banked in a research master cell bank (rMCB) which was stored in different locations. From this rMCB, working cell banks were prepared as follows: an ampoule of the rMCB was thawed, and the cells were propagated until enough cells were present to freeze the cells by using dry ice. Four hundred to 500 ampoules containing 1 ml ($1\text{-}2\times10^6$ cells/ml) of rMCB were stored in the vapor phase of a liquid nitrogen freezer.

PER.C6® Cell Preculture

One ampoule containing $5\times10^6$ PER.C6® cells of the WCB was thawed in a water bath at 37° C. Cells were rapidly transferred into a 50 ml tube and re-suspended by adding 9 ml of the suspension medium ExCell™ 525 (JRH Biosciences, Denver, Pa.) supplemented with 1×L-Glutamin. After three minutes of centrifugation at 1000 rpm, cells were re-suspended in a final concentration of $3\times10^5$ cells/ml and cultured in a T80 cm² tissue culture flask, at 37° C., 10% $CO_2$. Two to three days later, cells were seeded into 490 cm² tissue culture roller bottles (Corning Costar Corporation, Cambridge, Mass., US), with a density of $3\times10^5$/ml and cultured in continuous rotation at 1 rpm.

PER.C6® and MDCK Cell Culture

Madin Darby Canine Kidney (MDCK) cells were cultured in Dulbecco's modified Eagle's medium (DMEM, Life Technologies Breda, The Netherlands) containing 10% heat inactivated fetal bovine serum and 1×L-Glutamine (Gibco-BRL), at 37° C. and 10% $CO_2$.

Suspension cultures of PER.C6® were cultured in ExCell™ 525 (JRH Biosciences, Denver, Pa.) supplemented with 1×L-Glutamin, at 37° C. and 10% $CO_2$, in stationary cultures in six-well dishes (Greiner, Alphen aan de Rijn, The Netherlands) or in 490 cm² tissue culture roller bottles (Corning Costar Corporation, Cambridge, USA) during continuous rotation at 1 rpm.

Immunofluorescence Test

Direct immunofluorescence assays for the detection of influenza virus infection were carried out using the IMAGEN™ Influenza Virus A and B kit (DAKO, Glostrup, Denmark) according to the standard protocol of the supplier. Samples were viewed microscopically using epifluorescence illumination. Infected cells are characterized by a bright apple-green fluorescence.

Propidium Iodide Staining

Cell pellets were re-suspended into 300µ of cold PBS-0.5% BSA+5µ of propidium iodide 50 µg/ml in PBS-FCS-azide solution. Viable and dead cells were then detected via flow cytofluorometric analysis.

Hemagglutination Assay

To 50 µ/l of two-fold diluted virus solutions in PBS, 25 1/4 1 of a 1% suspension of turkey erythrocytes in PBS was added in 96-well microtiter plates and incubated at 4° C. for one hour. The hemagglutination pattern was examined, and expressed as hemagglutinating units (HAU). The amount of HAU corresponded to the reciprocal value of the highest virus dilution that showed complete hemagglutination.

PER.C6® Cells as Permissive Cell Line for Influenza A Virus

PER.C6® cells are not known for their ability to sustain influenza virus infection and replication. We, therefore, verified whether PER.C6® cells are permissive for influenza virus infection in comparison with MDCK (Madin Darby Canine Kidney) cells.

The day before infection, $2\times10^5$ MDCK cells/well were seeded in six-well plates. Twenty-four hours later, $4\times10^5$ PER.C6® cells/well and MDCK were infected with the H1N1 strain A/Puerto Rico/8/34 (titer $3.6\times10^7$ pfu/ml), obtained from Dr. Eric Claas, Dept. of Virology, Leiden University Medical Center, NL. Infection was performed at various multiplicities of infection ("MOIs") ranging from of 0.1 to 10 pfu/cell. After about two hours of incubation at 37° C., the inoculum was removed and replaced by fresh culture medium. A direct immunofluorescence assay for the detection of influenza virus infection was performed 24 and 48 hours post-infection. The experiment showed permissivity of PER.C6® cell for influenza infection, with percentages of positive cells moi-dependent and comparable with MDCK (see Table 1).

PER.C6® Cells as Cell Line for Influenza A Virus Propagation

Figure 2:
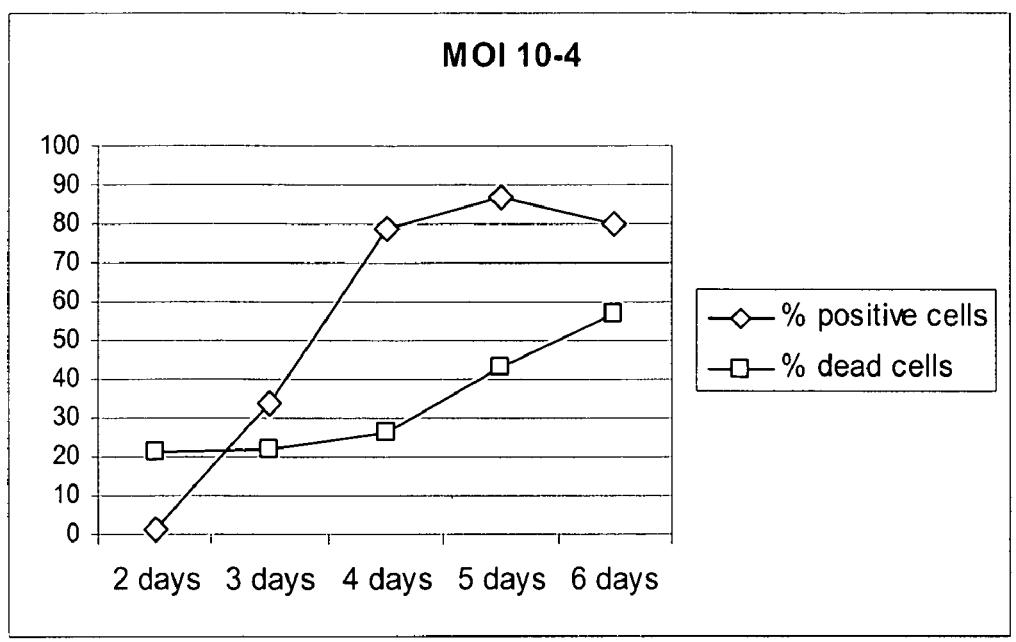
FIG. 2: Percentage of infected cells viewed microscopically after immunofluorescence assay. Samples derived from infection at moi 10 and 1, at 48 hours post-infection are not shown, because of full CPE.
Figure 2:
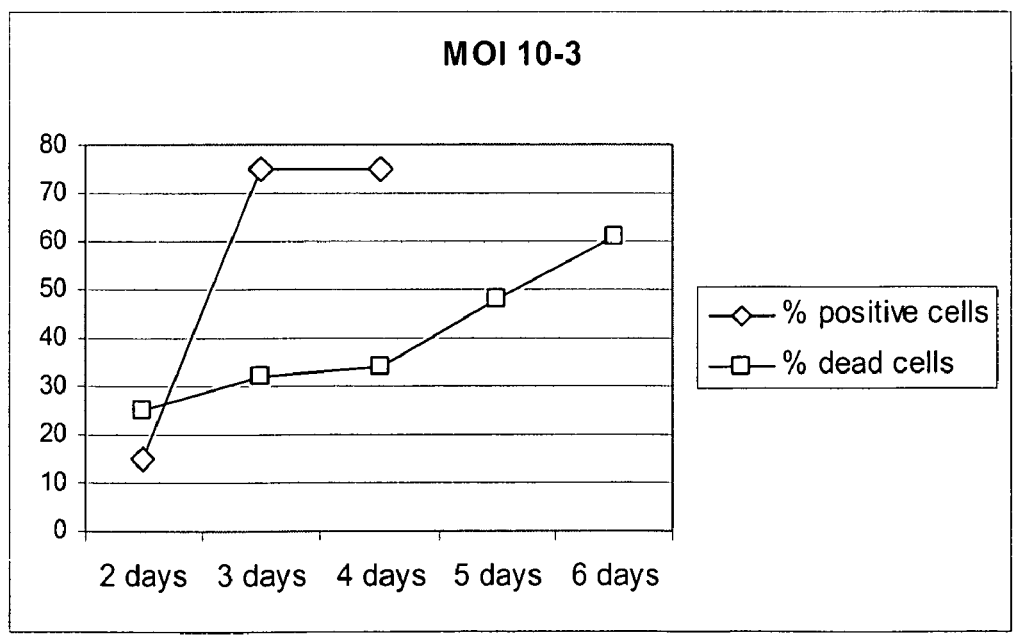
Figure 3:
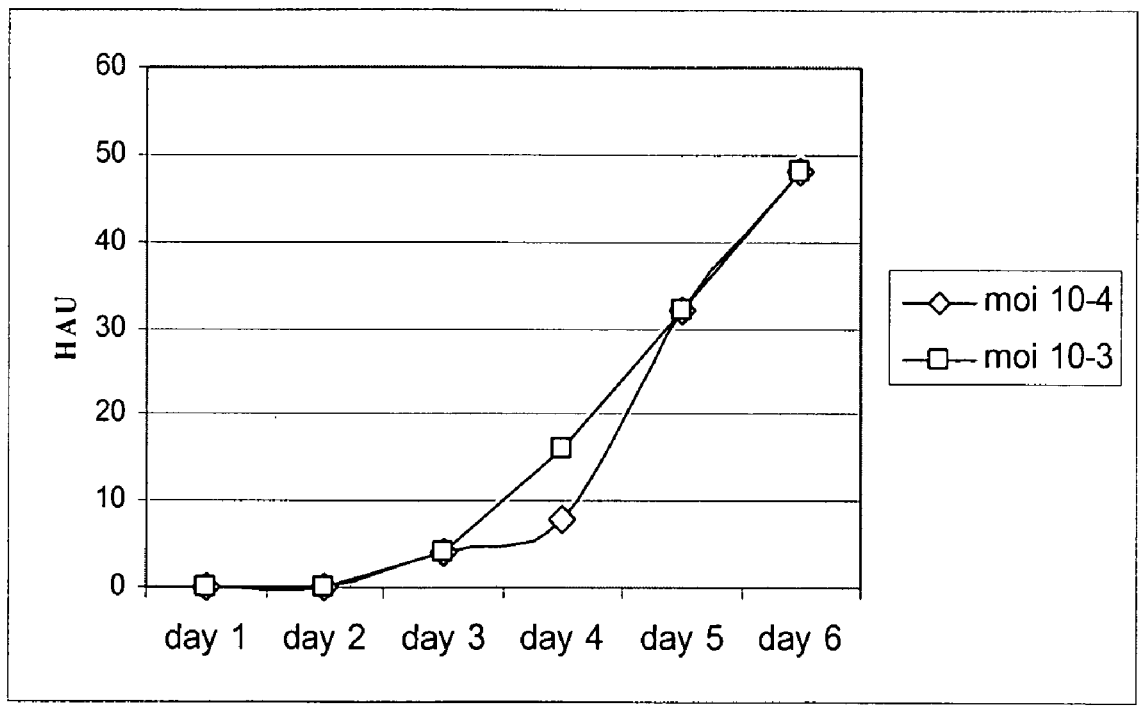
FIG. 3: Kinetics of virus propagation measured in hemagglutinating units (HAU) from day 1 to day 6 after infection.

We verified whether replication and propagation of influenza virus are supported by PER.C6® cells. The day of infection, PER.C6® cells were seeded in 490 cm² tissue culture roller bottles, with the density of $2\times10^5$ cells/ml in a final volume of 40 ml, in the presence of 5 µg/ml of trypsin-EDTA (Gibco-BRL). Cells were either mock inoculated or infected with the $H3N_2$ strain A/Shenzhen/227/95 (titer $1.5\times10^6$ pfu/ml), a kind gift from Dr. Eric Claas, Department of Virology, Leiden University Medical Center, NL. Infections were performed at moi $10^{-4}$ and $10^{-3}$ pfu/cell. After one hour of incubation at 37° C., the inoculum was removed by spinning down the cells at 1,500 rpm and re-suspending them in fresh culture medium +5 µg/ml of trypsin-EDTA. Harvest of 1.3 ml of cell suspension was carried out each day from day 1 to day 6 post-infection. Supernatants were stored at −80° C. and used for hemagglutination assays. Cell pellets were used for direct immunofluorescence tests and for propidium iodide staining (see FIG. 2).

Permissivity of PER.C6® Cell for Influenza Strains

Figure 4:
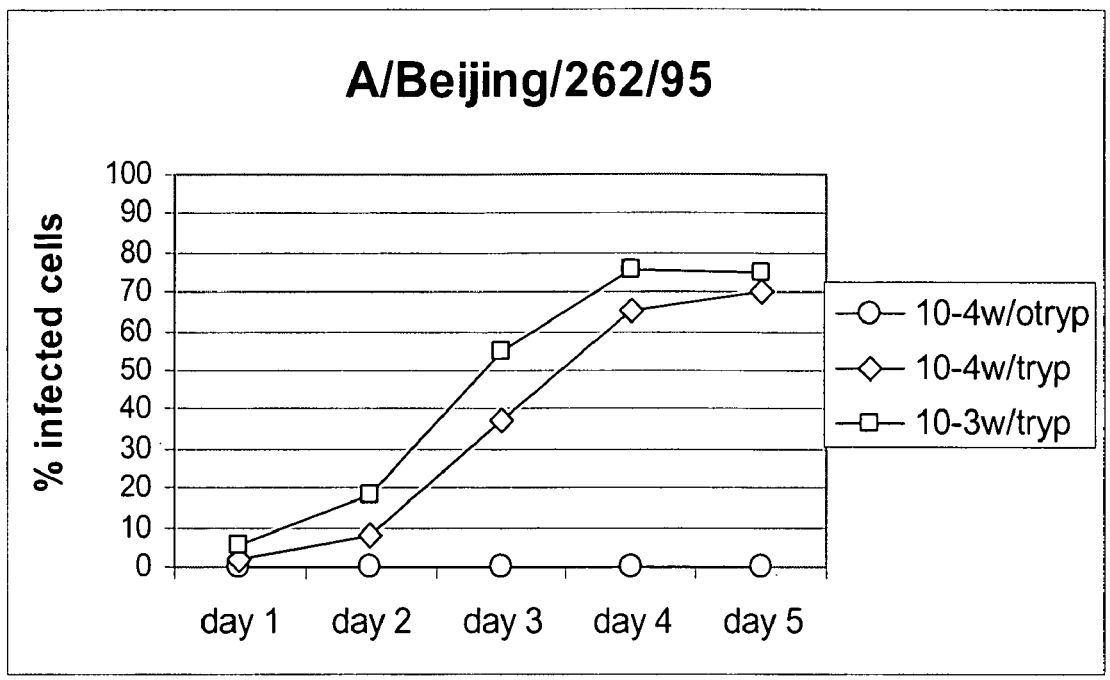
FIG. 4: Percentage of infected cells (positive cells) viewed microscopically after immunofluorescence assay.
Figure 4:
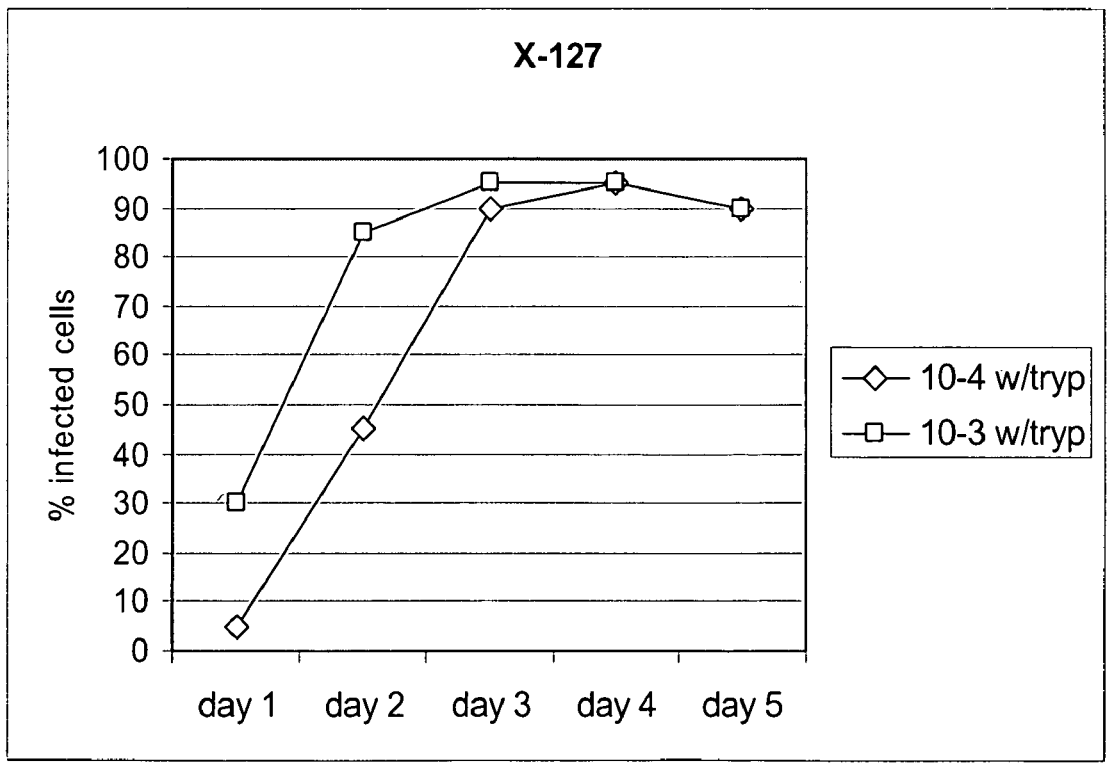
Figure 5:
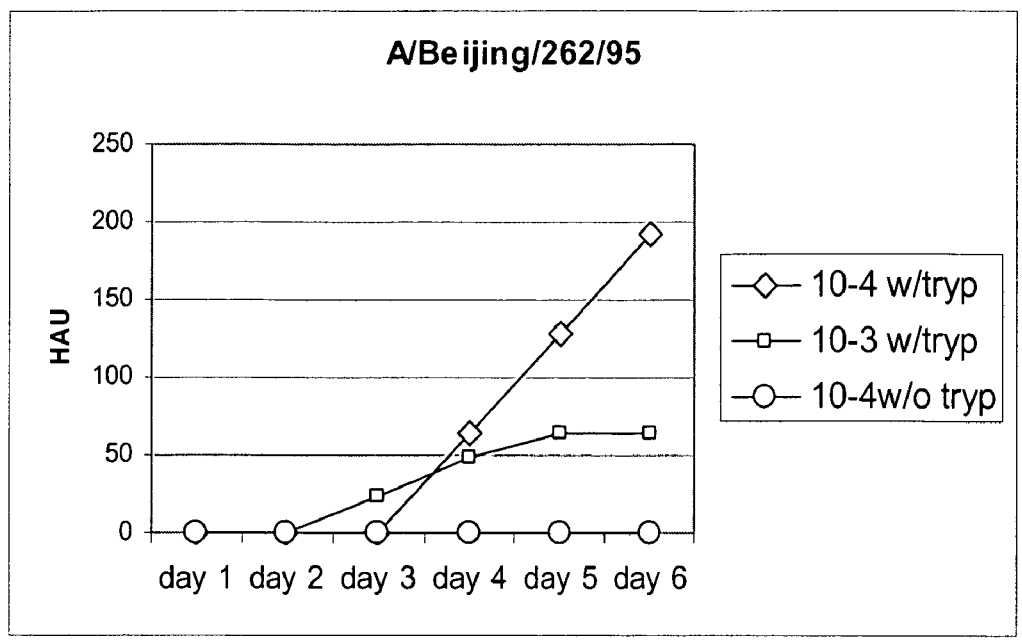
FIG. 5: Kinetics of virus propagation measured in hemagglutinating units (HAU) from day 1 to day 6 after infection.
Figure 5:
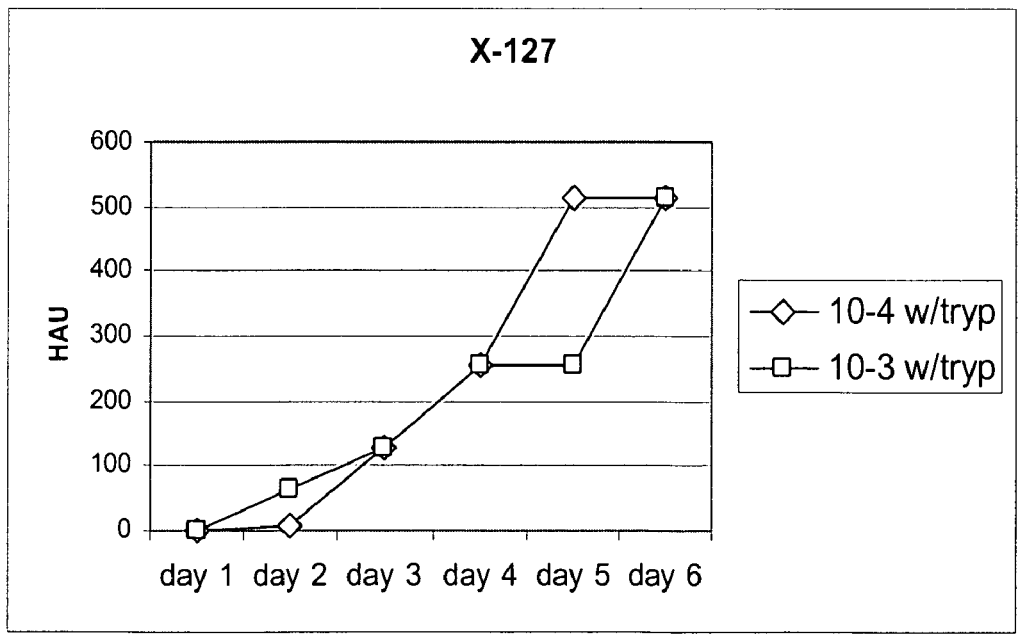

To further investigate the permissivity of PER.C6® cell for propagation of various influenza strains, we performed an infection by using the H1N1 vaccine strains A/Beijing/262/95 and its reassortant X-127 obtained from the National Institute for Biological Standards and Control (NIBSC), Potters Bar, UK. The day of infection, PER.C6® cells were seeded in 490 cm² tissue culture roller bottles, with the density of approximately $1\times10^6$ cells/ml in a final volume of 50 ml. Cells were inoculated with 5 µl (10-4 dilution) and 50 µl (10-3 dilution) of virus in the presence of 5 µg/ml trypsin-EDTA. In order to establish if trypsin was indeed required, one more infection was carried out by inoculating 5 µl of the strain A/Beijing/262/95 in the absence of the protease. After approximately one hour of incubation at 37° C., the inoculum was removed by spinning down the cells at 1,500 rpm and re-suspending them in fresh culture medium ±5 µg/ml of trypsin-EDTA. At day 2 and day 4 post-infection, more trypsin was added to the samples. Harvest of 1.3 ml of cell suspension was carried out from day 1 to day 6 post-infection. Supernatants were stored at −80° C. and used for hemagglutination assays and further infections; cell pellets were used for direct immunofluorescence tests. Results obtained with the above-mentioned immunofluorescence and hemagglutination assays are shown in FIGS. 4 and 5, respectively, illustrating the efficient replication and release of the viruses.

Infectivity of Virus Propagated on PER.C6® Cells

Figure 6:
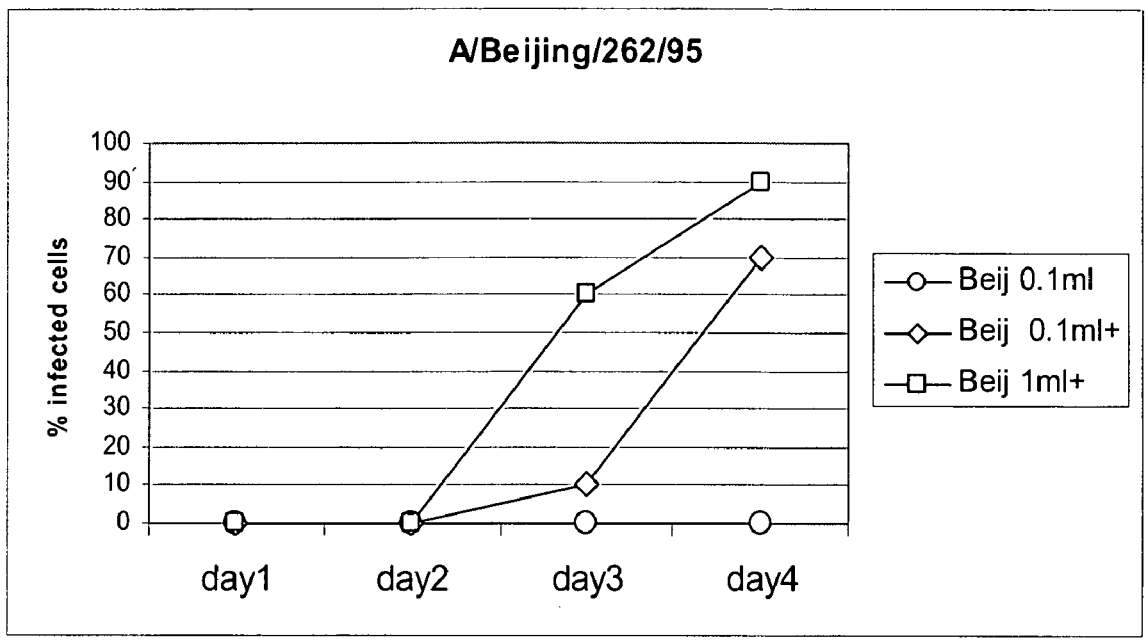
FIG. 6: Percentage of infected cells (positive cells) viewed microscopically after immunofluorescence assay.
Figure 6:
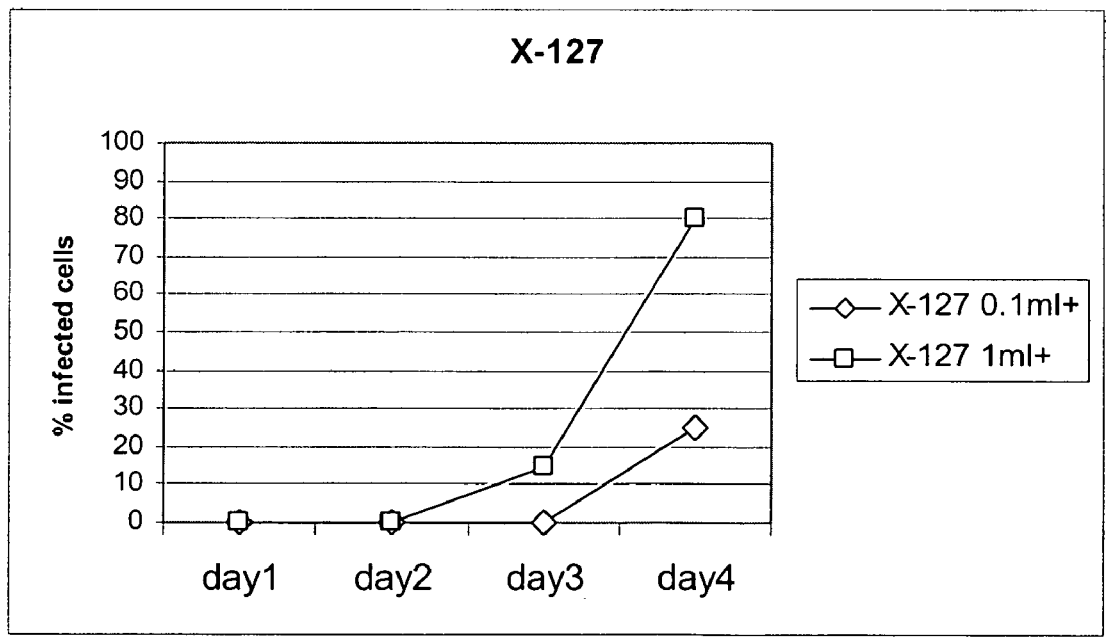
Figure 7:
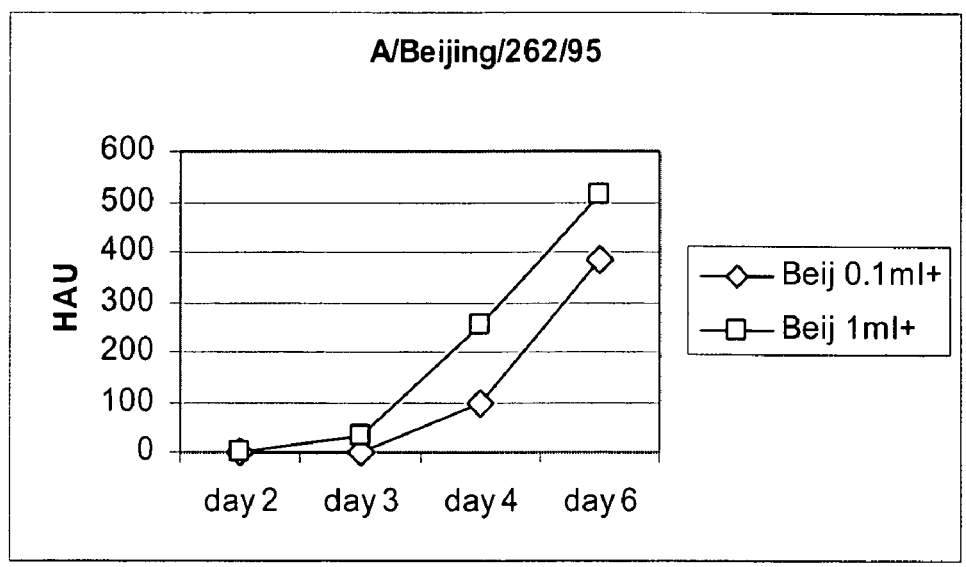
FIG. 7: Kinetics of virus propagation measured in hemagglutinating units (HAU) from day 2 to day 6 after infection.
Figure 7:
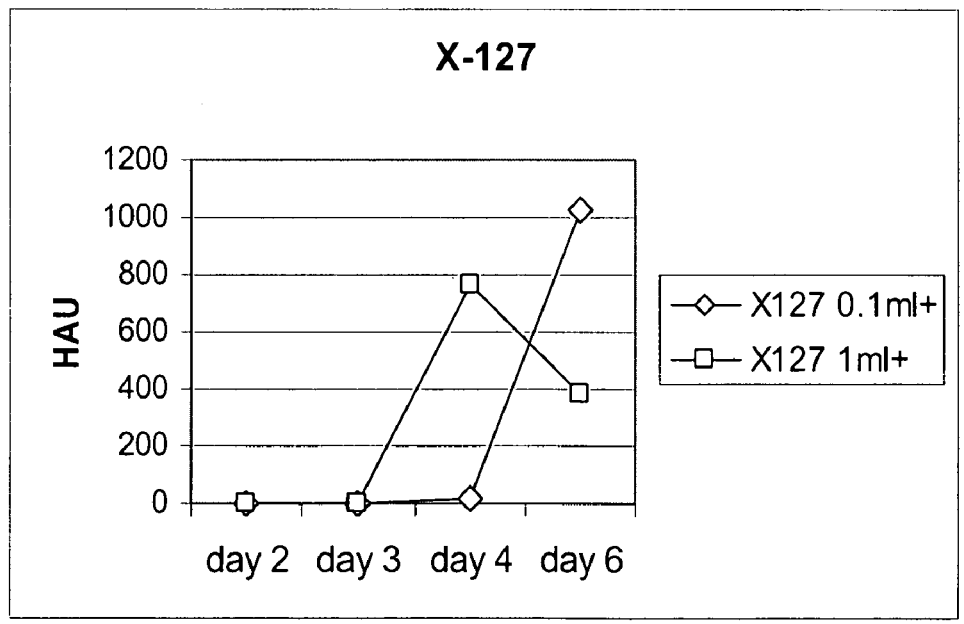

We verified if the viruses grown in PER.C6® cells were infectious and if adaptation to the cell line could increase virus yields. Virus supernatants derived from PER.C6® infected with the strains A/Beijing/262/95 and its reassortant X-127 (dil. 10-3) and harvested at day 6 post-infection, were used. At the day of infection, PER.C6® cells were seeded in 490 cm² tissue culture roller bottles, with the density of approximately $1\times10^6$ cells/ml in a final volume of 50 ml. Cells were inoculated with 100 µl and 1 ml of virus supernatant in the presence of 5 µg/ml trypsin-EDTA. In order to establish if trypsin was still required, one more infection was carried out by inoculating 100 µl of the strain A/Beijing/262/95 in the absence of the protease. After approximately one hour of incubation at 37° C., the inoculum was removed by spinning down the cells at 1,500 rpm and re-suspending them in fresh culture medium ±5 µg/ml of trypsin-EDTA. At day 2 and day 4 post-infection, more trypsin was added to the samples. Harvest of 1.3 ml of cell suspension was carried out from day 1 to day 6 post-infection. Supernatants were stored at −80° C. and used for hemagglutination assays and further infections; cell pellets were used for direct immunofluorescence tests. Results obtained with the above-mentioned immunofluorescence and hemagglutination assays are shown in FIGS. 6 and 7, respectively. Data obtained with the present experiment showed infectivity of the viruses grown in PER.C6® cells as well as an increase in virus yields.

Recovery of Virus

Intact virus is recovered from the culture medium by ion-exchange chromatography. The virus preparations are further processed to an inactivated surface antigen preparation by formaldehyde inactivation, solubilization with detergent and ultrafiltration and ultracentrifugation (H. Bachmayer, 1975).

REFERENCES

Bachmayer H. Selective solubilization of hemagglutinin and neuraminidase from influenza virus. *Intervirology* 1975; 5:260-272.

Brands R., A. M. Palache, and G. J. M. van Scharrenburg. Madin Darby Canine Kidney (MDCK) cells for the production of inactivated influenza subunit vaccine. Safety characteristics and clinical results in the elderly. In: L. E. Brown, E. W. Hampson, and R. G. Webster, editors. Option for the control of influenza III. Amsterdam, Elsevier, 1996; pp. 683-693.

Brands R., A. M. Palache, and G. J. M. van Scharrenburg. Development of influenza subunit vaccine produced using mammalian cell culture technology. M. J. T. Carrondo, B. Griffiths, and J. L. P. Moreira, editors. Animal cell technology: from vaccines to genetic medicine. Dordrecht: Kluwer Academic Publishers, 1997; pp. 165-167.

Gubareva L. V., J. M. Wood, W. J. Meyer, J. M. Katz, J. S. Robertson, D. Major, and R. G. Webster. Codominant mixtures of viruses in strains of influenza virus due to host cell variation. *Virol.* 1994; 199:89-97.

Herrero-Euribe L. et al. Replication of Influenza A and B viruses in human diploid cells. *J. Gen. Virol.* 1983; 64:471-475.

Kodihalli S., D. M. Justewicz, L. V. Gubareva, and R. G. Webster. Selection of a single amino acid substitution in the hemagglutinin molecule by chicken eggs can render influenza A virus (H3) candidate vaccine ineffective. *J. Virol.* 1995; 69:4888-4897.

Kirstner O., K. Muller, and C. Scholtissek. Differential phosphorylatian of the nucleoprotein of influenza A viruses. *J. Gen. Virol.* 1989; 70:2421-2431.

Murphy B. R. and R. G. Webster. Orthomyxoviruses. In: *Fields Virology*, chapter 46, 1397. Eds. B. N. Fields, D. M. Knipe, and P. M. Howley, et al. Lippincott-Raven Publishers, Philadelphia, Pa. 1996.

Newman R. W., R. Jenning, D. L. Major, J. S. Robertson, R. Jenkins, C. W. Potter, I. Burnett, L. Jewes, M. Anders, D. Jackson, and J. S. Oxford. Immune response of human volunteers and animals to vaccination with egg grown influenza A (H1N1) virus is influenced by three amino acid substitutions in the hemagglutinin molecule. *Vaccine*, 1993; 11:400-406.

Palache A. M., R. Brands, and G. J. M. van Scharrenburg. Immunogenicity and reactogenecity of influenza subunit vaccines produced in MDCK cells or fertilized chicken eggs. *J. Infert. Dis.* 1977; 176:S20-S23.

Robertson J. S., P. Cook, C. Nicolson, R. Newman, and J. M. Wood. Mixed populations in influenza vaccine strains. *Vaccine*, 1994; 12:1317-1320.

Robertson J. S., J. S. Bootman, C. Nicolson, D. Major, E. W. Robertson, and J. M. Wood. The hemagglutinin of influenza B virus present in clinical material is a single species identical to that of mammalian cell grown-virus. *Virol.* 1990; 179:35-40.

Robertson J. S., J. S. Bootman, R. Newman, J. S. Oxford, R. S. Daniels, R. G. Webster, and G. C. Schild. Structural changes in the hemagglutinin which accompany egg adaptation of an influenza A (H1N1) virus. *Virol.* 1987; 160:31-37.

Schild G. C., J. S. Oxford, J. C. de Jong, and R. G. Webster. Evidence for host-cell selection of influenza virus antigenic variants. *Nature*, 1983; 303:706-709.

Schulman J. L., and P. Palese. Virulence factors of influenza A viruses: WSN virus neuraminidase required for plaque production in MDBK cells. *J. Virol.* 1977; 24:170-176.

Sugiara A., and M. Ueda. Neurovirulence of influenza virus in mice. I. Neurovirulence of recombinants between virulent and avirulent virus strains. *Virol.* 1980; 101:440-449, 495, 271).

Tobita K., A. Sugiura, C. Enomoto, and M. Furuyama. Plaque assay and primary isolation of influenza A viruses in an established line of canine Kidney cells (MDCK) in the presence of trypsin. *Med. Microbiol. Immunol.* 1975; 162: 9-14.

Williams S. P., and J. S. Robertson. Analysis of restriction to the growth of non-egg-adapted human influenza in eggs. *Virol.* 1993; 196:660665.

---

What is claimed is:

1. An immortalized human embryonic retinoblast cell expressing a gene product of adenoviral E1A gene and a gene product of adenoviral E1B gene, wherein, the cell comprises complete viral RNA of an influenza virus.

2. The cell of claim 1, wherein the cell is a PER.C6® cell as deposited under ECACC number 96022940, which cell has been provided with nucleic acid encoding an influenza virus.

3. The cell of claim 2, wherein the cell has been provided with nucleic acid encoding an influenza virus by infection with the influenza virus.

4. A cell culture comprising the cell of claim 1 and a culture medium, and wherein the culture medium further comprises influenza virus.

5. The cell culture of claim 4, wherein the culture medium is free of serum.

* * * * *

SEQUENCE LISTING

<160> NUMBER OF SEQ ID NOS: 1

<210> SEQ ID NO 1
<211> LENGTH: 3052
<212> TYPE: DNA
<213> ORGANISM: adenoviridae
<220> FEATURE:
<221> NAME/KEY: misc_feature
<222> LOCATION: (1)..(3052)
<223> OTHER INFORMATION: adenovirus serotype 5 (Ad5) E1A and E1B coding
      sequences (Ad5 nucleotides 459-3510)

<400> SEQUENCE: 1
cgtgtagtgt atttataccc ggtgagttcc tcaagaggcc actcttgagt gccagcgagt      60
agagttttct cctccgagcc gctccgacac cgggactgaa aatgagacat attatctgcc     120

-continued

```
acggaggtgt tattaccgaa gaaatggccg ccagtctttt ggaccagctg atcgaagagg      180
tactggctga taatcttcca cctcctagcc attttgaacc acctacccTt cacgaactgt      240
atgatttaga cgtgacggcc cccgaagatc ccaacgagga ggcggtttcg cagattTttc      300
ccgactctgt aatgttggcg gtgcaggaag ggattgactt actcactttt ccgccggcgc      360
ccggttctcc ggagccgcct cacctttccc ggcagcccga gcagccggag cagagagcct      420
tgggtccggt ttctatgcca aaccttgtac cggaggtgat cgatcttacc tgccacgagg      480
ctggcttTcc acccagtgac gacgaggatg aagagggtga ggagtttgtg ttagattatg      540
tggagcaccc cgggcacggt tgcaggtctt gtcattatca ccggaggaat acgggggacc      600
cagatattat gtgttcgctt tgctatatga ggacctgtgg catgtttgtc tacagtaagt      660
gaaaattatg ggcagtgggt gatagagtgg tgggtttggt gtggtaattt ttttttttaat      720 ttttacagtt ttgtggttta agaattttTg tattgtgatt ttttTaaaag gtcctgtgtc      780
tgaacctgag cctgagcccg agccagaacc ggagcctgca agacctaccc gccgtcctaa      840
aatggcgcct gctatcctga gacgcccgac atcacctgtg tctagagaat gcaatagtag      900
tacggatagc tgtgactccg gtccttctaa cacacctcct gagatacacc cggtggtccc      960
gctgtgcccc attaaaccag ttgccgtgag agttggtggg cgtcgccagg ctgtggaatg     1020
tatcgaggac ttgcttaacg agcctgggca acctttggac ttgagctgta aacgccccag     1080
gccataaggt gtaaacctgt gattgcgtgt gtggttaacg cctttgtttg ctgaatgagt     1140
tgatgtaagt ttaataaagg gtgagataat gtttaacttg catggcgtgt taaatggggc     1200
ggggcttaaa gggtatataa tgcgccgtgg gctaatcttg gttacatctg acctcatgga     1260
ggcttgggag tgtttggaag attttTctgc tgtgcgtaac ttgctggaac agagctctaa     1320
cagtacctct tggtttTgga ggtttctgtg gggctcatcc caggcaaagt tagtctgcag     1380
aattaaggag gattacaagt gggaatttga agagcttttg aaatcctgtg gtgagctgtt     1440
tgattctTTg aatctgggtc accaggcgct ttTccaagag aaggtcatca agactttgga     1500
ttttTccaca ccggggcgcg ctgcggctgc tgttgctttT ttgagtttTta taaggataa      1560 atggagcgaa gaaacccatc tgagcggggg gtacctgctg gattttctgg ccatgcatct     1620
gtggagagcg gttgtgagac acaagaatcg cctgctactg ttgtcttccg tccgcccggc     1680
gataataccg acggaggagc agcagcagca gcaggaggaa gccaggcggc ggcggcagga     1740
gcagagccca tggaacccga gagccggcct ggaccctcgg gaatgaatgt tgtacaggtg     1800
gctgaactgt atccagaact gagacgcatt ttgacaatta cagaggatgg gcaggggcta     1860
aagggggtaa agagggagcg ggggcttgt gaggctacag aggaggctag gaatctagct      1920
tttagcttaa tgaccagaca ccgtcctgag tgtattactt ttcaacagat caaggataat     1980
tgcgctaatg agcttgatct gctggcgcag aagtattcca tagagcagct gaccacttac     2040
tggctgcagc caggggatga ttTtgaggag gctattaggg tatatgcaaa ggtggcactt     2100
aggccagatt gcaagtacaa gatcagcaaa cttgtaaata tcaggaattg ttgctacatt     2160
tctgggaacg gggccgaggt ggagatagat acggaggata gggtggcctt tagatgtagc     2220
atgataaata tgtggccggg ggtgcttggc atggacgggg tggttattat gaatgtaagg     2280
tttactggcc ccaattttag cggtacggtt ttcctggcca ataccaacct tatcctacac     2340
```

-continued

```
ggtgtaagct tctatgggtt taacaatacc tgtgtggaag cctggaccga tgtaagggtt   2400
cggggctgtg ccttttactg ctgctggaag ggggtggtgt gtcgccccaa aagcagggct   2460
tcaattaaga aatgcctctt tgaaaggtgt accttgggta tcctgtctga gggtaactcc   2520
agggtgcgcc acaatgtggc ctccgactgt ggttgcttca tgctagtgaa aagcgtggct   2580
gtgattaagc ataacatggt atgtggcaac tgcgaggaca gggcctctca gatgctgacc   2640
tgctcggacg gcaactgtca cctgctgaag accattcacg tagccagcca ctctcgcaag   2700
gcctggccag tgtttgagca taacatactg acccgctgtt ccttgcattt gggtaacagg   2760
aggggggtgt tcctacctta ccaatgcaat ttgagtcaca ctaagatatt gcttgagccc   2820
gagagcatgt ccaaggtgaa cctgaacggg gtgtttgaca tgaccatgaa gatctggaag   2880
gtgctgaggt acgatgagac ccgcaccagg tgcagaccct gcgagtgtgg cggtaaacat   2940
attaggaacc agcctgtgat gctggatgtg accgaggagc tgaggcccga tcacttggtg   3000
ctggcctgca cccgcgctga gtttggctct agcgatgaag atacagattg ag           3052
```